US010172984B2

(12) United States Patent
Locke et al.

(10) Patent No.: US 10,172,984 B2
(45) Date of Patent: Jan. 8, 2019

(54) REDUCED-PRESSURE TREATMENT AND DEBRIDEMENT SYSTEMS AND METHODS

(75) Inventors: Christopher Brian Locke, Bournemouth (GB); Timothy Mark Robinson, Basingstoke (GB); Amy K. McNulty, Stillwater, MN (US)

(73) Assignee: KCI Licensing, Inc., San Antonio, TX (US)

( * ) Notice: Subject to any disclaimer, the term of this patent is extended or adjusted under 35 U.S.C. 154(b) by 1291 days.

(21) Appl. No.: 13/588,747

(22) Filed: Aug. 17, 2012

(65) Prior Publication Data

US 2013/0053793 A1 Feb. 28, 2013

Related U.S. Application Data

(60) Provisional application No. 61/529,510, filed on Aug. 31, 2011.

(51) Int. Cl.
| | | |
|---|---|---|
| *A61M 35/00* | (2006.01) | |
| *A61M 1/00* | (2006.01) | |
| A61F 13/00 | (2006.01) | |
| A61M 1/36 | (2006.01) | |
| A61M 27/00 | (2006.01) | |

(52) U.S. Cl.
CPC ......... *A61M 1/0088* (2013.01); *A61M 1/0031* (2013.01); *A61M 1/3687* (2013.01); *A61M 27/00* (2013.01); *Y10T 137/0402* (2015.04)

(58) Field of Classification Search
CPC .. A61M 1/0088; A61M 1/0031; A61M 27/00; A61M 1/3687
USPC ................................................. 604/290, 304
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |

(Continued)

FOREIGN PATENT DOCUMENTS

| | | |
|---|---|---|
| AU | 550575 A1 | 8/1982 |
| AU | 745271 | 4/1999 |

(Continued)

OTHER PUBLICATIONS

International Search Report and Written Opinion for corresponding PCT Application No. PCT/US2012/051410 dated Nov. 28, 2012.

(Continued)

*Primary Examiner* — Andrew J Mensh (57) ABSTRACT

A reduced-pressure treatment system for debriding a treatment area of a tissue site and applying reduced pressure is disclosed. The reduced-pressure treatment system includes a hydrogel having a blocked acid debriding agent. The hydrogel is adapted to cover the treatment area and enhance autolytic debridement at the treatment area. The reduced-pressure treatment system includes a manifold that is adapted to cover the hydrogel and distribute reduced pressure to the tissue site. The reduced-pressure treatment system also includes a sealing drape for forming a fluid seal over the tissue site and manifold. Other systems, methods, and dressings are presented.

25 Claims, 8 Drawing Sheets

(56) References Cited

U.S. PATENT DOCUMENTS

| | | |
|---|---|---|
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,569,742 B2 * | 8/2009 | Haggstrom et al. ............ 602/53 |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0091601 A1 * | 5/2003 | Barbul ................ A61K 31/198 424/400 |
| 2005/0175665 A1 * | 8/2005 | Hunter et al. ................ 424/423 |
| 2006/0052416 A1 * | 3/2006 | Dickson et al. ............. 514/314 |
| 2010/0331797 A1 * | 12/2010 | Patel et al. .................... 604/319 |
| 2014/0163491 A1 | 6/2014 | Schuessler et al. |
| 2015/0080788 A1 | 3/2015 | Blott et al. |

FOREIGN PATENT DOCUMENTS

| | | |
|---|---|---|
| AU | 455496 | 2/2002 |
| CA | 2005436 | 6/1990 |
| CA | 2841160 A1 | 1/2013 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | 80/02182 | 10/1980 |
| WO | 87/04626 | 8/1987 |
| WO | 90/010424 | 9/1990 |
| WO | 93/009727 | 5/1993 |
| WO | 94/020041 | 9/1994 |
| WO | 96/05873 | 2/1996 |
| WO | 97/18007 | 5/1997 |
| WO | 99/13793 | 3/1999 |

(56) References Cited

FOREIGN PATENT DOCUMENTS

| WO | WO2007030601 A2 | 3/2007 | |
|---|---|---|---|
| WO | WO2008040020 A2 | 4/2008 | |
| WO | 2009152374 A2 | 12/2009 | |
| WO | WO 2009152374 A2 * | 12/2009 | ............ A61K 31/19 |
| WO | WO2010/025219 A1 | 3/2010 | |
| WO | 2013032745 A1 | 3/2013 | |

OTHER PUBLICATIONS

N.A. Bagautdinov, "Variant of External Vacuum Aspiration in the Treatment of Purulent Diseases of the Soft Tissues," Current Problems in Modem Clinical Surgery: Interdepartmental Collection, edited by V. Ye Volkov et al. (Chuvashia State University, Cheboksary, U.S.S.R. 1986);pp. 94-96 (certified translation).

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", the Lancet, Sep. 3, 1983, pp. 532-534.

Chinn, Steven D. et al.: "Closed Wound Suction Drainage", the Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovic, V. Ð ukić, Ž. Maksimović, Ð . Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax, "Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

Japanese Notice of Rejection corresponding to Application No. 2016128285, dated May 9, 2017.

Chinese First Office Action corresponding to Application No. 2012800403711, dated Aug. 19, 2015.

Chinese Second Office Action corresponding to Application No. 2012800403711, dated May 9, 2016.

(56) References Cited

OTHER PUBLICATIONS

Zhang, Xueying "The Role Arginine Plays in Repairing the Trauma of Organism"; Shanghai Prevention Medicine Journal, pp. 426-428, vol. 19, No. 8, 2007, published Dec. 31, 2007.
Zheng, Junmin "Medicinal Polymer Material", China Medical Science Press, pp. 94-96, published Jan. 31, 2009.
Chinese Decision of Rejection for corresponding Application No. 2012800403711, dated Dec. 5, 2016.
Canadian Examiner's Report for corresponding Application No. 2842958, dated Jun. 20, 2018.

* cited by examiner

REDUCED-PRESSURE TREATMENT AND DEBRIDEMENT SYSTEMS AND METHODS

RELATED APPLICATIONS

The present invention claims the benefit, under 35 USC § 119(e), of the filing of U.S. Provisional Patent Application Ser. No. 61/529,510, entitled "Reduced-Pressure Treatment and Debridement Systems and Methods," filed Aug. 31, 2011, which is incorporated herein by reference for all purposes.

FIELD

The present disclosure relates generally to medical treatment systems and, more particularly, but not by way of limitation, to reduced-pressure treatment and debridement systems and methods.

BACKGROUND

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue.

SUMMARY

According to an illustrative embodiment, a reduced-pressure treatment system for debriding a treatment area of a tissue site is disclosed. The reduced-pressure treatment system includes a hydrogel that is adapted to cover the treatment area. The hydrogel includes a blocked acid debriding agent. The reduced-pressure treatment system includes a manifold that is adapted to cover the hydrogel and distribute reduced pressure to the tissue site. The reduced-pressure treatment system also includes a sealing drape for placing over, and forming a fluid seal over, the tissue site and manifold.

According to an illustrative embodiment, a method of manufacturing a reduced-pressure wound dressing for treating a tissue site and debriding a treatment area is provided. The method comprises a step of providing a hydrogel that includes a blocked acid debriding agent and is adapted to cover the treatment area. The method of manufacturing includes a step of providing a manifold that is adapted to cover the hydrogel and distribute reduced pressure to the tissue site. The method of manufacturing also includes a step of providing a sealing drape for placing over the tissue site and manifold. The sealing drape is adapted to form a fluid seal over the tissue site and manifold.

According to an illustrative embodiment, a method for treating a tissue site on a patient is also provided. The method includes the steps of defining a treatment area by applying a hydrogel to a portion of the tissue site, wherein the treatment area comprises tissue to be debrided. The method includes a step of applying a manifold over the hydrogel. The manifold is adapted to deliver reduced pressure to the tissue site. The method includes a step of applying a sealing drape over the tissue site and manifold to form a fluid seal over the tissue site and manifold, as well as a step of providing reduced pressure to the manifold.

According to an illustrative embodiment, a reduced-pressure wound dressing is disclosed. The reduced-pressure wound dressing includes a hydrogel that is adapted to cover a treatment area of a tissue site, and the hydrogel comprises a blocked acid debriding agent. The reduced-pressure wound dressing also includes a manifold that is adapted to cover the hydrogel and distribute reduced pressure to the tissue site. Further, the reduced-pressure wound dressing includes a sealing drape for placing over the tissue site and manifold. The sealing drape is adapted to form a fluid seal over the tissue site and manifold.

Other features and advantages of the illustrative embodiments will become apparent with reference to the drawings and detailed description that follow.

DETAILED DESCRIPTION OF ILLUSTRATIVE EMBODIMENTS

In the following detailed description of the illustrative, non-limiting embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
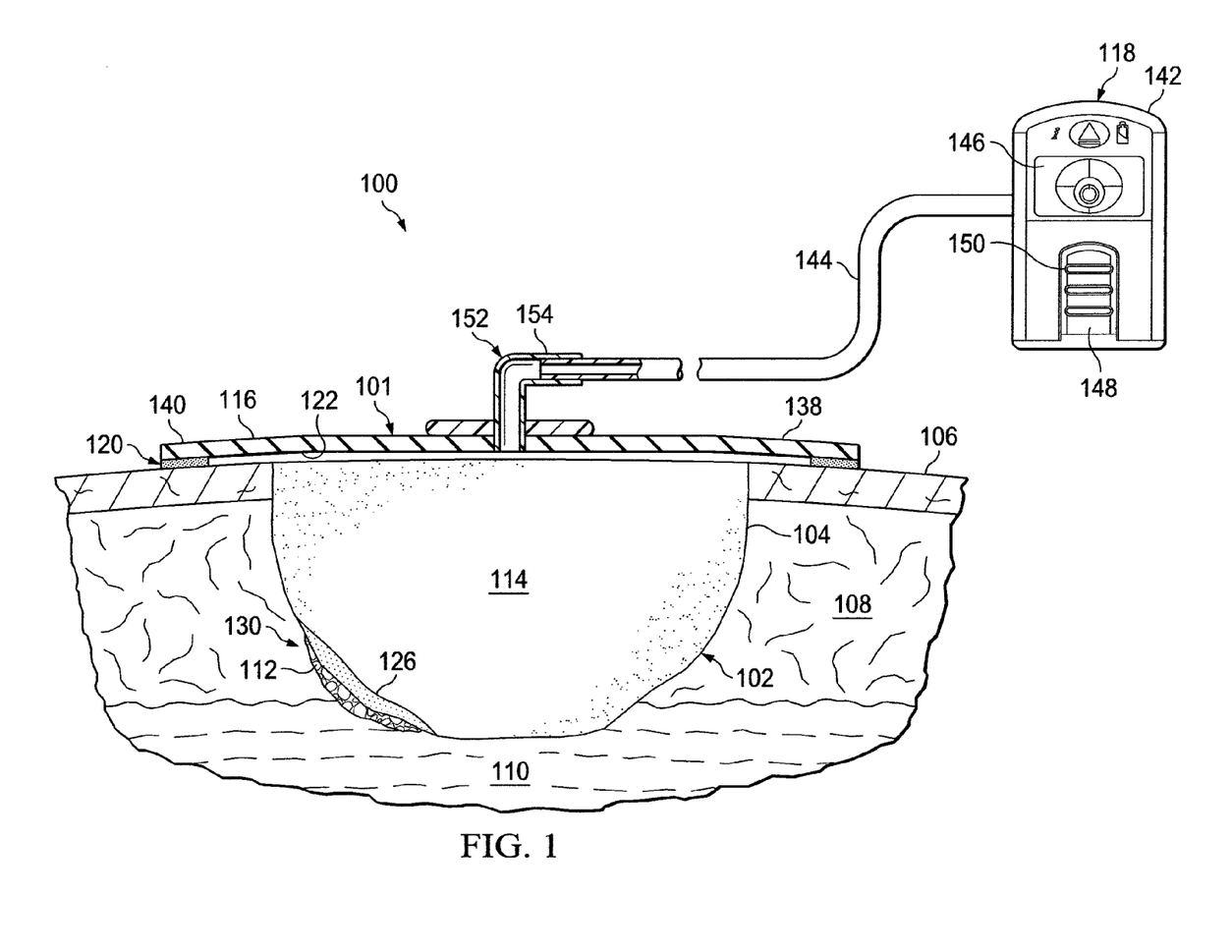
FIG. 1 is a schematic, side view, with a portion shown in cross section, of a reduced-pressure treatment system employing enhanced autolytic debridement to remove necrotic tissue from a wound.

Referring now primarily to FIG. 1, a reduced-pressure treatment system 100 for treating a tissue site 102, e.g., a wound 104, is presented. Whether the etiology of a wound, or damaged area of tissue, is trauma, surgery, or another cause, proper care of the wound, or wounds, is important to the outcome. The wound 104 may include, without limitation, any irregularity with a tissue, such as an open wound, surgical incision, or diseased tissue. The reduced-pressure treatment system 100 is presented in the context of a tissue site 102 that includes the wound 104, which is through the epidermis 106, or generally skin, and the dermis 108 and reaching into a hypodermis, or subcutaneous tissue 110. The reduced-pressure treatment system 100 may be used to treat a wound of any depth, as well as many different types of wounds including open wounds or other tissue sites. The tissue site 102 may be the bodily tissue of any human, animal, or other organism, including bone tissue, adipose tissue, muscle tissue, dermal tissue, vascular tissue, connective tissue, cartilage, tendons, ligaments, or any other tissue. Treatment of the tissue site 102 may include removal of fluids, e.g., exudate or ascites. Unless otherwise indicated, as used herein, "or" does not require mutual exclusivity.

The wound 104 may include necrotic tissue 112, and in many instances, it may be desirable to remove the necrotic tissue 112 in order to promote healing of the wound 104. The illustrative, non-limiting embodiment shows the reduced-pressure treatment system 100 in the context of the wound 104 having a localized, or discrete area, of necrotic tissue 112 within the wound. The reduced-pressure treatment system 100 may be used in broader contexts, including with any tissue site having undesirable tissue. Such undesirable tissue may include, necrotic, damaged, infected, contaminated, or adherent tissue, foreign material within the wound 104, and may include a layer of necrotic tissue 112 that covers the entire surface of the wound 104. At the same time, it is desirable to apply reduced pressure to the wound 104.

The reduced-pressure treatment system 100 includes a reduced-pressure wound dressing 101 and a reduced-pressure subsystem 118. The reduced-pressure wound dressing 101 includes a manifold 114 and a sealing drape 116. The reduced-pressure wound dressing 101 may also include an attachment device 120 that affixes the sealing drape 116 to the epidermis 106 of the patient. The sealing drape 116 may also include an adhesive surface that seals directly against the epidermis 106 of the patient without the need for an attachment device. The manifold 114 is positionable between a tissue-facing surface 122 of the sealing drape 116 and the tissue site 102.

The manifold 114 is a substance or structure that is provided to assist in applying reduced pressure to, delivering fluids to, or removing fluids from a tissue site 102. The manifold 114 typically includes a plurality of flow channels or pathways that distribute fluids provided to and removed from the tissue site 102 around the manifold 114. In one illustrative embodiment, the flow channels or pathways are interconnected to improve distribution of fluids provided or removed from the tissue site 102. The manifold 114 may be a biocompatible material that is capable of being placed in contact with the tissue site 102 and distributing reduced pressure to the tissue site 102 and may include, without limitation, devices that have structural elements arranged to form flow channels, such as, for example, cellular foam, open-cell foam, porous tissue collections, liquids, gels, and foams that include, or cure to include, flow channels; foam, gauze; felted mat; or any other material suited to a particular biological application. In one embodiment, the manifold 114 is a porous foam and includes a plurality of interconnected cells or pores that act as flow channels. The porous foam may be a polyurethane, open-cell, reticulated foam such as GranuFoam® material manufactured by Kinetic Concepts, Incorporated of San Antonio, Tex. In some situations, the manifold 114 may also be used to distribute fluids such as medications, antibacterials, growth factors, and various solutions to the tissue site 102. Other layers may be included in or on the manifold 114, such as absorptive materials, wicking materials, hydrophobic materials, and hydrophilic materials.

In one illustrative, non-limiting embodiment, the manifold 114 may be constructed from a bioresorbable material that may remain in a patient's body following use of the reduced-pressure wound dressing 101. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The manifold 114 may further serve as a scaffold for new cell-growth, or a scaffold material may be used in conjunction with the manifold 114 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The reduced-pressure wound dressing 101 includes a hydrogel 126 preferably having a blocked acid debriding agent. The hydrogel 126 is applied over a treatment area 130 that includes necrotic tissue 112. Here, "treatment area" refers to the portion of the tissue site that is covered by the hydrogel 126. The hydrogel 126 assists in the debridement of the necrotic tissue 112 for the purpose of improving wound health. In an illustrative, non-limiting embodiment, the hydrogel 126 includes a blocked acid debriding agent. The hydrogel 126 may be formed from a variety of water soluble or swellable polymers, such as gums (e.g., xanthan and guar), or cellulose (e.g., carboxymethyl and hydroxy celluloses), or other synthetic polymers (e.g., polyvinyl alcohols, polyvinyl pyrrolidones, and carboxy or hydroxy modified acrylics and polyurethanes). In one embodiment, the hydrogel may be formed by slurrying together a poloxamer and carboxymethylcellulose in propylene glycol, then adding water. The slurry may be mixed at a high velocity and air bubbles can be removed from the mixture using a centrifuge. One or more debriding agents can be added to the gel mixture as desired.

As used herein, the terms "debride," "debriding," and "debridement," relate to the act of removing or the removal of undesirable tissue, such as, eschar, necrotic, damaged, infected, contaminated, or adherent tissue, or foreign material from a tissue site. Several methods of debridement may be employed to treat a wound 104 having necrotic tissue 112, including surgical debridement, mechanical debridement, chemical debridement, and autolytic debridement.

Chemical, or enzymatic, debridement entails the use of chemical enzymes to convert the necrotic tissue to slough. Chemical debridement may be fast-acting and cause minimal damage to healthy tissue if the chemicals are applied properly. But, chemical debridement has disadvantages as well. The process may be expensive and traditional chemical debridement methods and systems, such as low pH systems, may be painful to a patient. Other debriding agents, such as papain, may have other health implications and only have limited usage that is restricted by law. Other agents may be used, such as medical grade honey, but may show limited efficacy and can become quickly mobile in the presence of fluid, such as wound exudate, and an applied negative pressure.

Autolytic debridement, or autolysis, entails the use of the body's own enzymes and white blood cells, along with moisture, to hydrate and liquefy the necrotic tissue 112 and slough. Since autolytic debridement is a naturally occurring process, it is relatively painless and does not risk damage to healthy tissue. Further, autolytic debridement does not require wound fluid to remain in contact with the necrotic tissue 112, and can be facilitated by the use of films, hydrocolloids, and hydrogels. A disadvantage of autolytic debridement is that autolytic debridement is slower than other types of debridement, rendering the wound susceptible to infection.

There is a need for a debriding process that accelerates, and thereby enhances, the naturally-occurring debridement process. Moreover, it is desirable to have a system and method that allow reduced-pressure treatment to occur. Further still, reducing the pain experienced by a patient remains desirable. The debridement systems and methods corresponding to the illustrative, non-limiting embodiments of FIGS. 1-8 enhance debridement and healing of wounds. The enhanced autolytic debridement systems and methods described herein provide a low or reduced-pain alternative to traditional debridement methods that can be used in conjunction with reduced-pressure treatment, while still employing the beneficial aspects of autolytic debridement.

In an embodiment, the hydrogel 126 facilitates the removal of necrotic tissue 112 from the wound 104 under reduced pressure. The hydrogel 126 is adapted to enhance autolytic debridement by preserving or creating a moist environment at the treatment area 130. In some cases, the hydrogel 126 may further enhance the natural debridement process by introducing a debriding agent, such as a blocked acid debriding agent, to the treatment area 130.

The hydrogel material is a combination of water and a polymer that preserves a moist environment at the tissue site 102 where the hydrogel 126 is applied. Since the hydrogel 126 is in direct contact with the treatment area 130, the hydrogel may be hydrophilic, and adapted to absorb wound exudate. The absorptive properties of the hydrogel 126 keep the treatment area 130 moist while preventing excess fluid from accumulating at the tissue site 102. The hydrogel 126 may also rehydrate the tissue site 102, including slough or necrotic tissue 112 at the treatment area 130 to enhance the autolytic debridement process. Other beneficial characteristics of the hydrogel material are that the hydrogel material may generally be gas permeable and does not adhere to the tissue site 102. Thus, removal of the hydrogel 126 will not damage the tissue site 102 or treatment area 130, or cause pain to the patient.

Since the hydrogel 126 is generally non-porous, the hydrogel 126 may isolate the treatment area 130, including necrotic tissue 112, from the manifold 114. By isolating the necrotic tissue 112, the hydrogel 126 prevents reduced pressure from being transmitted by the manifold 114 to the treatment area 130. The ability of the hydrogel 126 to prevent reduced pressure from being applied to a particular location may be beneficial. If a treatment area 130 is particularly sensitive, then isolating the treatment area 130 with the hydrogel 126 can allow a caregiver to apply reduced-pressure to the majority of a tissue site 102 while not applying reduced pressure to the sensitive portion of the wound.

The hydrogel 126 may also have an osmotic effect on the wound 104. In some embodiments, the hydrogel 126 creates an osmotic pressure that draws fluid out of the wound 104 at the treatment area 130, thereby facilitating a moist environment at the treatment area 130 that is conducive to autolytic debridement. The osmotic pressure may result from the ionic content of the hydrogel 126 or the hydrogel 126 comprising a fluid absorbing material (e.g., a water soluble material). In either case, an osmotic pressure motivates moisture across the tissue surface.

In cases where additional moisture is desired, the caregiver may place an additional semi-permeable membrane (not shown) in contact with the treatment area 130 underneath the hydrogel 126. For example, a membrane with a salt on one side may create an additional osmotic pressure and motivate fluid to move across the tissue surface at the treatment area 130 into the hydrogel 126.

Figure 2:
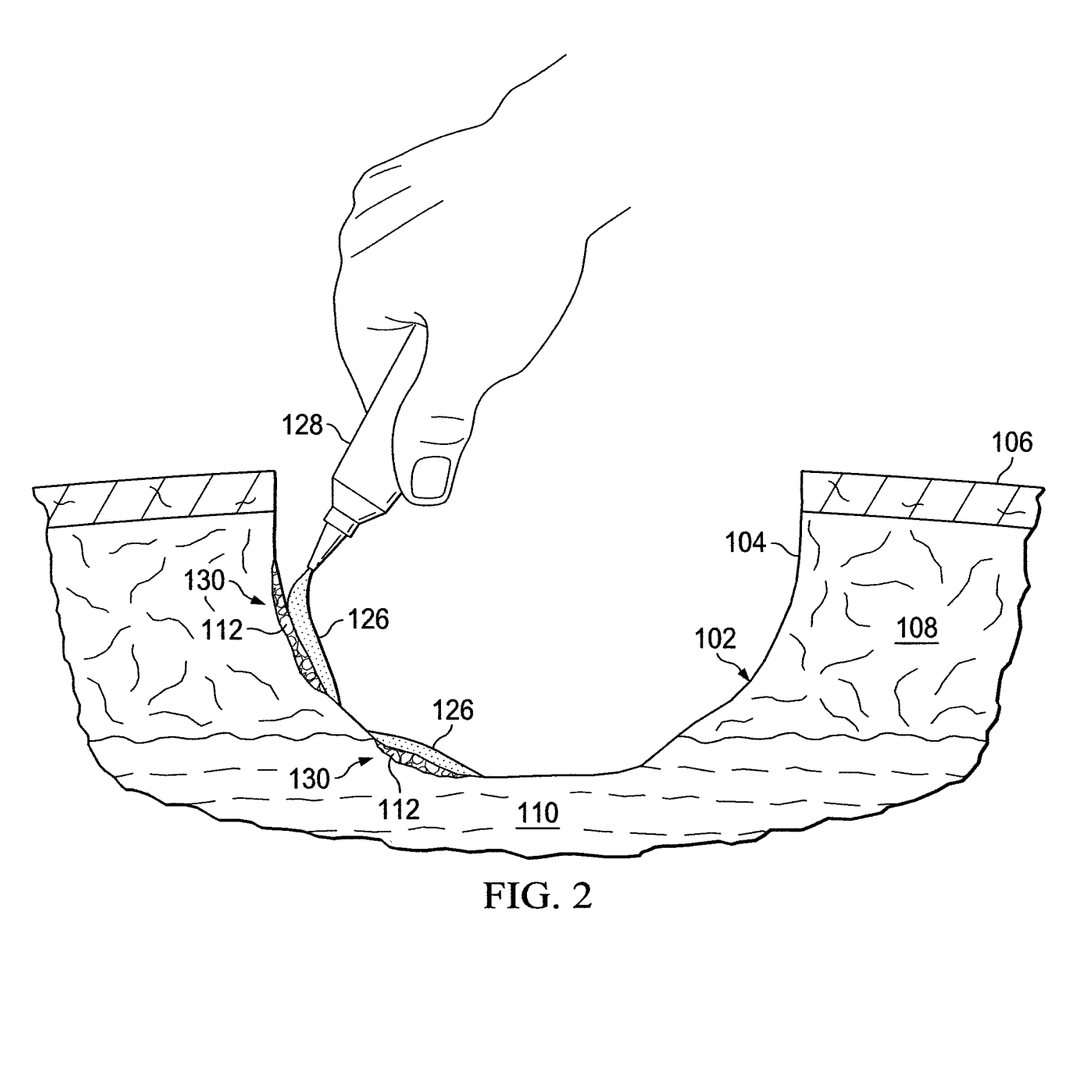
FIG. 2 is a schematic, side perspective view, with a portion shown in cross section, of a wound bed having necrotic tissue that shows the application of a blocked acid debriding agent to the wound bed.
Figure 3:
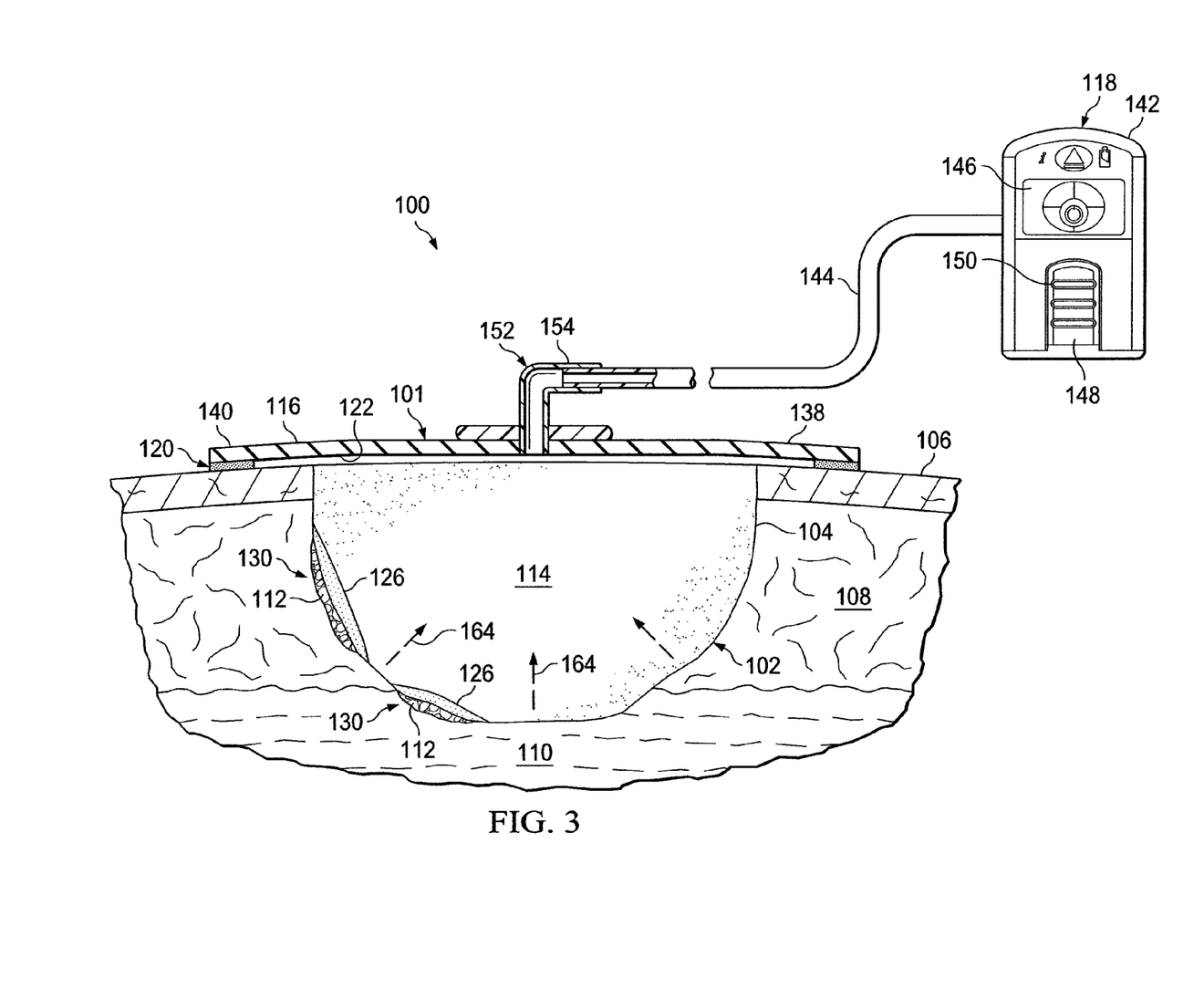
FIG. 3 is a schematic, side view, with a portion shown in cross section, of a wound bed being treated by the reduced-pressure treatment system of FIG. 1.

The hydrogel 126 may be an amorphous hydrogel applied in gel form from a tube 128, as shown in FIG. 2, or other applicator. Alternatively, the hydrogel 126 may be a flexible sheet or one or more strips of casted hydrogel. If the hydrogel 126 is a pre-formed sheet, the sheet forming the hydrogel 126 may be peeled from a non-stick backing and manually applied to the treatment area 130 by a caregiver. The non-stick layer may be desirable to prevent the hydrogel from sticking to the caregiver during application. The fabrication of the hydrogel 126 may be manipulated to result in hydrogels of varying stiffness, ranging from a viscous gel to a flexible sheet.

Figure 5:
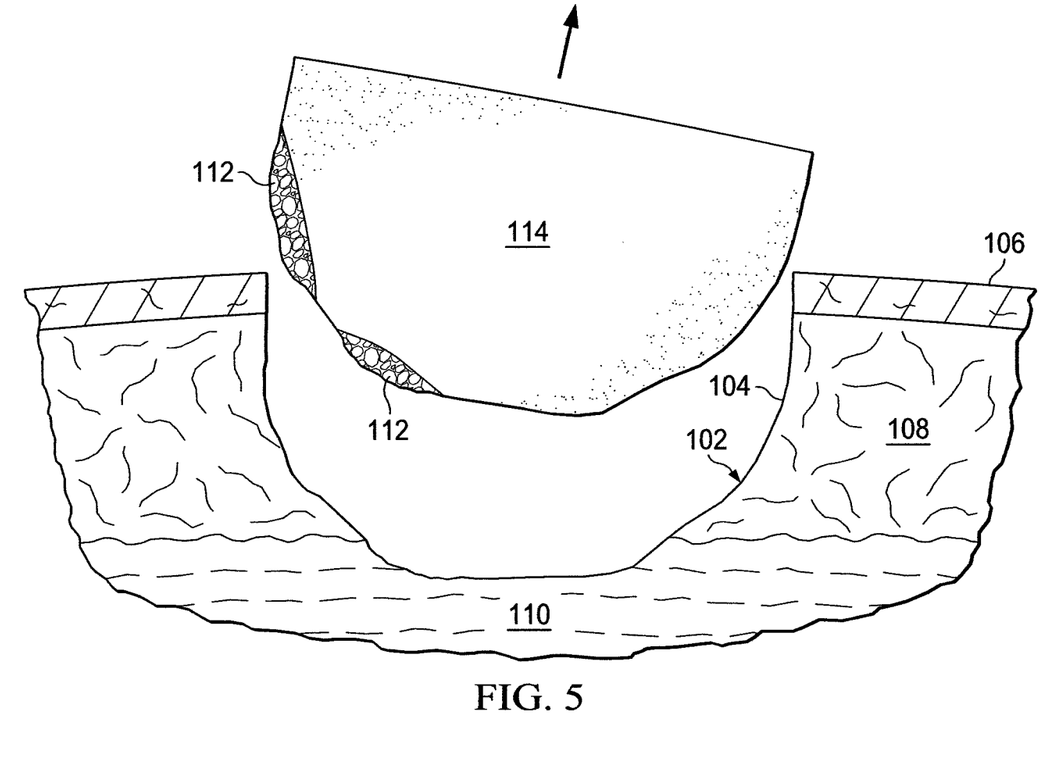
FIG. 5 is a schematic cross section, of a wound bed at the conclusion of treatment by the reduced-pressure treatment system of FIG. 1.

As the hydrogel 126 is exposed to and absorbs wound fluids over time, the hydrogel 126 will soften or become less viscous. Under reduced pressure over time, the softened hydrogel 126 will lose structural integrity, break apart, be absorbed into the manifold 114, and be removed from the tissue site 102 by the reduced-pressure subsystem 118. Similarly, as the necrotic tissue 112 softens, pathways may form in the necrotic tissue 112 and hydrogel 126 that allow the debrided necrotic tissue 112 and hydrogel 126 to be pulled into the foam pores of the manifold 114. The debrided necrotic tissue 112 may then be evacuated from the tissue site 102 by the reduced-pressure source 142, or drawn into the manifold 114 and removed with the reduced-pressure wound dressing 101, as shown in FIG. 5. Similarly, the necrotic tissue 112 may be liquefied by the debridement process in some cases and drawn through the manifold 114 into a wound fluid collection canister 148, of the reduced-pressure source 142. This method of debridement allows necrotic tissue 112 to be pulled away under moist conditions, which is less painful to the patient.

In some embodiments, the hydrogel 126 may be formulated to withstand moisture and reduced pressure for a relatively longer time period before softening and being absorbed by the manifold. For example, the wound 104 may be better treated using a hydrogel that does not soften and break apart until after a relatively longer debridement process has occurred. As non-limiting examples, the hydrogel may not soften and break apart for one day, two days, three days, four days, five days, six days, seven days, eight days, or even longer. Stiffer, or higher viscosity, compositions of hydrogels will have a higher initial resistance to softening and decomposition. In addition, many properties of the hydrogel 126, such as viscosity and the speed at which the hydrogel material softens, can be controlled by varying the moisture that is initially in the hydrogel. Thus, by varying the moisture that is in the hydrogel before the hydrogel is placed in the wound 104 (e.g., at the time of fabrication), the hydrogel may be made to remain intact within the wound 104 to enhance autolytic debridement for a preselected time period. A stiffer low-water-content hydrogel will take longer to reach a given water content (and hence to a given viscosity) than a hydrogel containing a higher level of water. The hydrogel may also be crosslinked to a higher level to provide a higher viscosity, and the crosslinking will also reduce the rate of water uptake by controlling the amount of swell the polymer in the hydrogel can accommodate.

Given that reduced pressure is supplied to the manifold 114 over the hydrogel 126, another effect of the gradual softening and removal of the hydrogel 126 and debrided necrotic tissue 112 is that the treatment area 130 that was covered by the hydrogel 126 is gradually exposed to reduced pressure as the debridement process concludes. Initially, the hydrogel 126 blocks the transmission of reduced pressure to the treatment area 130 by clogging the pores of the manifold 114 at the interface with the hydrogel 126. As the hydrogel 126 softens and breaks apart, portions of the hydrogel 126 are pulled into manifold 114 and drawn away from the tissue site 102 under reduced pressure. As a result, the previously covered treatment area 130 is gradually exposed to reduced pressure. Other means may also function to control the rate at which reduced pressure is supplied to the tissue site 102. In addition to using a relatively stiffer hydrogel, the manifold 114 may be formed with smaller pores. The manifold 114 with smaller pores will remain blocked by the hydrogel 126 for a longer period because the hydrogel 126 will not permeate the smaller pores until the hydrogel 126 has undergone further softening.

In another embodiment, a perforated film (not shown) can be used to adjust the rate at which reduced pressure is applied to the previously-covered portion of the tissue site 102. The film may be a polyurethane or poly-vinyl material that does not dissolve. The film may also be a biodegradable material such as a polyglucanate (PGA). In addition, the perforated film may be used in conjunction with various hydrogel compositions (e.g. a stiffer hydrogel composition) to control the rate at which the hydrogel layer 126 breaks apart. Use of the perforated film along with a stiffer hydrogel composition may also control the rate at which additional portions of the treatment area 130 are exposed to reduced pressure. For example, a perforated film of a biodegradable material may be used with a relatively stiffer hydrogel to delay the rate at which reduced pressure is applied to the treatment area 130.

The hydrogel 126 material may also include one or more debriding agents, such as papain, subtilysin, bromain, collagenase, ficin, pepsin, trypsin, chymotrypsin, elastase, enzymes isolated from any suitable insect larvae, or one or more analogues thereof. In addition, the hydrogel 126 may include a blocked acid debriding agent. The blocked acid debriding agent may be an alpha hydroxy acid. The alpha hydroxy acid may be a glycolic acid or a lactic acid, which typically has a low pH, and may be loosely bound to a blocking material, such as an arginine amino group. Various alpha hydroxy acids in combination with arginine, when mixed into a composition such as the hydrogel 126 detailed above, are able to show significant effectiveness as debriding agents. Such blocked acid debriding agents do not have a pH that is vastly different from the pH of a typical wound, and therefore are less likely to cause pain and discomfort to the patient.

Typically, the pH of open wounds is slightly alkaline or neutral, in the range of 6.5-8.5. As the wound heals, the pH tends toward that of normal skin (approximately 5.9). Conversely, compositions containing alpha hydroxy acids that may be used as debriding agents may have pH values that are substantially lower. For example, typical formulations containing 7.6% glycolic acid or 9% lactic acid each have a pH of 1.9. Exposure of the relatively high pH wound to the compositions of lower pH can cause irritation and discomfort. In the interest of patient comfort, it is desirable to utilize a hydrogel material that does not subject the treatment area 130 to a debriding agent having too low a pH.

The use of a blocked/complexed acid debriding agent in the hydrogel 126 moderates the rate at which the debriding agent interacts with the necrotic tissue 112. If the same debriding agent, for example, a glycolic or lactic acid, were to be applied directly to the necrotic tissue 112, the magnitude and rate of the change in pH at the treatment area 130 would be significant and likely cause pain and irritation to the patient. The blocked acid debriding agent is formed by loosely binding a blocking agent or complexing agent, such as arginine, to a debriding agent, such as alpha hydroxy acid. In the presence of wound fluid, the blocked acid debriding agent will slowly disassociate, thereby gradually supplying debriding agent to the treatment area 130 without causing an abrupt change in pH at the treatment area 130. Accordingly, the rate at which the change in pH is applied to the treatment area 130 may be regulated by the blocking agent. The slower pH change helps to avoid a stinging sensation for the patient.

The hydrogel 126 may comprise the blocked acid debriding agent. The blocked acid debriding agent has the effect of moderating the rate of decrease of the pH of the treatment area 130 as the hydrogel 126 interacts with the necrotic tissue. When applied, the pH of the hydrogel 126 may be within 50% (e.g., within 40%, 30%, 20%, 10%, 5%, 4%, 3%, 2%, 1%, or any number within the stated range) of the pH of a typical wound bed. For example, the hydrogel 126 with the blocked acid debriding agent may have an initial pH of about 3.5. As the hydrogel 126 absorbs water and reacts with necrotic tissue, the pH of the hydrogel 126 would increase towards 7. This assumes that the wound bed has an initial pH of 7 (a "healthy" wound bed could be as low as 6 and chronic wound bed could be greater than 8).

The hydrogel 126 may be formed to have blocked acid debriding agent in an amphoteric composition. The amphoteric composition contains at least one alpha hydroxy acid, such as lactic acid or glycolic acid. The hydrogel with amphoteric composition has a pH closer to the pH of the wound than a similar non-amphoteric hydrogel, and can gradually release the active form of the alpha hydroxy acid into the treatment area 130 as a debriding agent.

Amphoteric substances are substances that have the characteristics of both an acid and a base, and may be inorganic or organic compounds. An organic amphoteric compound molecule, for example, comprises at least one basic group and one (anionic) acidic group. A cationic group may include an amino group (e.g., arginine), or an imino or guanido group. An acidic group may include a carboxylic group, phosphoric group or a sulfonic group. Examples of organic amphoteric compounds include amino acids, peptides, polypeptides, proteins, and creatine. Further examples include aminoaldonic acids, aminouronic acids, lauryl aminopropylglycine, aminoaldaric acids, neuraminic acid, desulfated heparin, deacetylated hyaluronic acid, hyalobiuronic acid, chondrosine and deacetylated chondroitin. Zinc oxide and aluminum oxide are examples of inorganic amphoteric compounds.

The amphoteric composition may be, for example, an alpha hydroxy acid (e.g., glycolic or lactic acid) combined with a cationic compound (e.g., arginine). Use of an amphoteric composition containing the alpha hydroxy acid may be beneficial because the overall pH of the composition is raised. The raised pH is closer to the pH of the treatment area 130, which results in less irritation and related discomfort when the debriding agent comes into contact with the treatment area 130. In addition, some alpha hydroxy acid molecules react with the amphoteric compound to form an ionic complex that may act as buffering system to control the release of free (undissociated) alpha hydroxy acid into the treatment area 130. The buffering system further limits irritation and discomfort while still retaining effectiveness as a debriding agent.

The amphoteric composition is formulated as a hydrogel. The hydrogel incorporates an amphoteric compound and one of the alpha hydroxy acids or related compounds. The compounds may be dissolved, for example, in a mixture of ethanol, water and propylene glycol in a volume ratio of 40:40:20, respectively. The mixture includes 0.1 to 4 percent gelling agent such as methyl cellulose, ethyl cellulose, hydroxyethylcellulose, hydroxypropylcellulose, hydroxypropylmethylcellulose, carbomer or ammoniated glycyrrhizinate that is added with agitation.

A first example of an amphoteric composition contains 1M 2-hydroxyethanoic acid and 0.5M L-arginine in solution form, and may be formulated as follows: 2-Hydroxyethanoic acid (glycolic acid) 7.6 g is dissolved in water 60 ml and propylene glycol 20 ml. L-Arginine 8.7 g is added to the solution with stirring until all the crystals are dissolved. Ethanol is added to make the total volume of the solution 100 ml. The amphoteric composition thus formulated has pH 3.0. An amphoteric composition formulated from 1M 2-hydroxyethanoic acid and 1M L-arginine has pH 6.3. The solution has pH 1.9 if no amphoteric compound is incorporated.

A second amphoteric composition contains 1M 2-hydroxypropanoic acid and 0.5M L-arginine in solution form, and may be formulated somewhat similarly: 2-Hydroxypropanoic acid (DL-lactic acid) USP grade 9.0 g is dissolved in water 60 ml and propylene glycol 20 ml. L-Arginine 8.7 g is added to the solution with stirring until all the crystals are dissolved. Ethanol is added to make the total volume of the solution 100 ml. The amphoteric composition thus formulated has pH 3.1. An amphoteric composition formulated from 1M 2-hydroxypropanoic acid and 1M L-arginine has pH 6.9. The solution has pH 1.9 if no amphoteric compound is incorporated.

Referring again primarily to FIG. 1, the sealing drape 116 includes a first surface 140 and the tissue-facing surface 122. The sealing drape 116 may be sized so that the sealing drape 116 overlaps the wound 104 in such a manner that a drape extension 138 extends beyond the periphery of the wound 104. The sealing drape 116 may be any material that provides a fluid seal. The sealing drape 116 may be, for example, an impermeable or semi-permeable, elastomeric material. For semi-permeable materials, the permeability must be low enough that for a given reduced-pressure source, the desired reduced pressure may be maintained. The sealing drape 116 may be any material that provides a fluid seal, which maintains reduced pressure at a desired site given the particular reduced-pressure source or subsystem involved.

The attachment device 120 may be used to hold the sealing drape 116 against the patient's epidermis 106 or another layer, such as a gasket or additional sealing drape. The attachment device 120 may take numerous forms. For example, the attachment device 120 may be a medically-acceptable, pressure-sensitive adhesive that extends about a periphery, a portion of, or the entire sealing drape 116. As additional examples, the attachment device 120 may be a double-sided drape tape, paste, hydrocolloid, hydrogel, or other sealing devices or elements.

The reduced-pressure subsystem 118 includes a reduced-pressure source 142, which can take many different forms. The reduced-pressure source 142 provides reduced pressure as a part of the reduced-pressure treatment system 100. Reduced pressure references a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Unless otherwise indicated, values of pressure stated herein are gauge pressures. The reduced pressure delivered may be static, dynamic (patterned or random) and may be delivered continuously or intermittently. Consistent with the use herein, an increase in reduced pressure or vacuum pressure typically refers to a relative reduction in absolute pressure.

The reduced-pressure subsystem 118 provides reduced pressure. The reduced-pressure subsystem 118 includes the reduced-pressure source 142 that may be any means of supplying a reduced pressure. The reduced-pressure source 142 may be any device for supplying a reduced pressure, such as a vacuum pump, wall suction, micro-pump, or other source. If a micro-pump is utilized, it may be included in or on the dressing 101 itself.

While the amount and nature of reduced pressure applied to a tissue site will typically vary according to the application, the reduced pressure will typically be between −5 mm Hg (−667 Pa) and −500 mm Hg (−66.7 kPa) and more typically between −75 mm Hg (−9.9 kPa) and −300 mm Hg (−39.9 kPa). For example, and not by way of limitation, the pressure may be −12, −12.5, −13, −13.5, −14, −14.5, −15, −15.5, −16, −16.5, −17, −17.5, −18, −18.5, −19, −19.5, −20, −20.5, −21, −21.5, −22, −22.5, −23, −23.5, −24, −24.5, −25, −25.5, −26, −26.5 kPa or another pressure.

In the illustrative, non-limiting embodiment of FIG. 1, the reduced-pressure source 142 has a battery compartment 146 and a canister 148 with windows 150 providing a visual indication of the level of fluid within canister 148. An interposed membrane filter, such as a hydrophobic or oleophobic filter, may be inserted between the reduced-pressure conduit 144 and the reduced-pressure source 142.

The reduced pressure provided by the reduced-pressure source 142 is delivered through the reduced-pressure conduit 144 to a reduced-pressure interface 152, which may be an elbow port 154. In one illustrative embodiment, the reduced-pressure interface 152 is a T.R.A.C.® Pad or Sensa T.R.A.C.® Pad available from KCI of San Antonio, Tex. The reduced-pressure interface 152 allows the reduced pressure to be delivered to the sealing drape 116 and realized within an interior portion of sealing drape 116 and the manifold 114. In this illustrative, non-limiting embodiment, the elbow port 154 extends through the sealing drape 116 to the manifold 114, but numerous arrangements are possible.

According to one illustrative embodiment, in operation, the hydrogel 126 is applied as will be described further below, and the manifold 114 is placed proximate to the tissue site 102, e.g., wound 104. The manifold 114 may be placed within the wound 104, or may overlay a portion of the wound 104. The sealing drape 116 may be placed over the manifold 114 such that the drape extension 138 extends beyond the periphery of the wound 104. The drape extension 138 may be secured to the patient's epidermis 106 by the attachment device 120 in order to form a fluid seal between the patient's epidermis 106 and the sealing drape 116.

The reduced-pressure interface 152 may then be applied, if not already installed, and the reduced-pressure conduit 144 fluidly coupled to the reduced-pressure interface 152.

The reduced-pressure interface 152 may also be omitted and the reduced-pressure conduit 144 may be directly inserted into the manifold 114. The reduced-pressure conduit 144 is fluidly coupled to the reduced-pressure source 142. The reduced-pressure source 142 may then be activated to deliver reduced pressure to the interior of the sealing drape 116 and manifold 114. In another embodiment, the reduced-pressure source 142 may be a micro-pump in or on the dressing 101.

With regard to the illustrative system of FIG. 1, the application of reduced pressure ensures close proximity of the hydrogel 126 to the necrotic tissue 112. When reduced pressure is supplied to the manifold 114, the manifold 114 transmits the reduced pressure to the wound 104 surrounding the treatment area 130, which is drawn inward toward the manifold 114 as indicated by arrows 164 in FIG. 3. In turn, the treatment area 130 and associated necrotic tissue 112 are compressed against the hydrogel 126, ensuring that the hydrogel 126 will provide a moist environment to enhance autolytic debridement.

The debriding process may cause the wound 104 including the treatment area 130 to generate an increased amount of exudate. The presence of the hydrogel 126 may also cause an increase in wound exudate. The reduced-pressure treatment system 100 is operable to evacuate exudate by drawing exudate through the manifold 114 to the canister 148 of the reduced-pressure source 142. In addition to preventing excess amounts of fluid from remaining in the wound, the application of reduced pressure to remove fluids also functions to reduce the level of toxins at the wound site that may occur with autolytic debridement.

Figure 4:
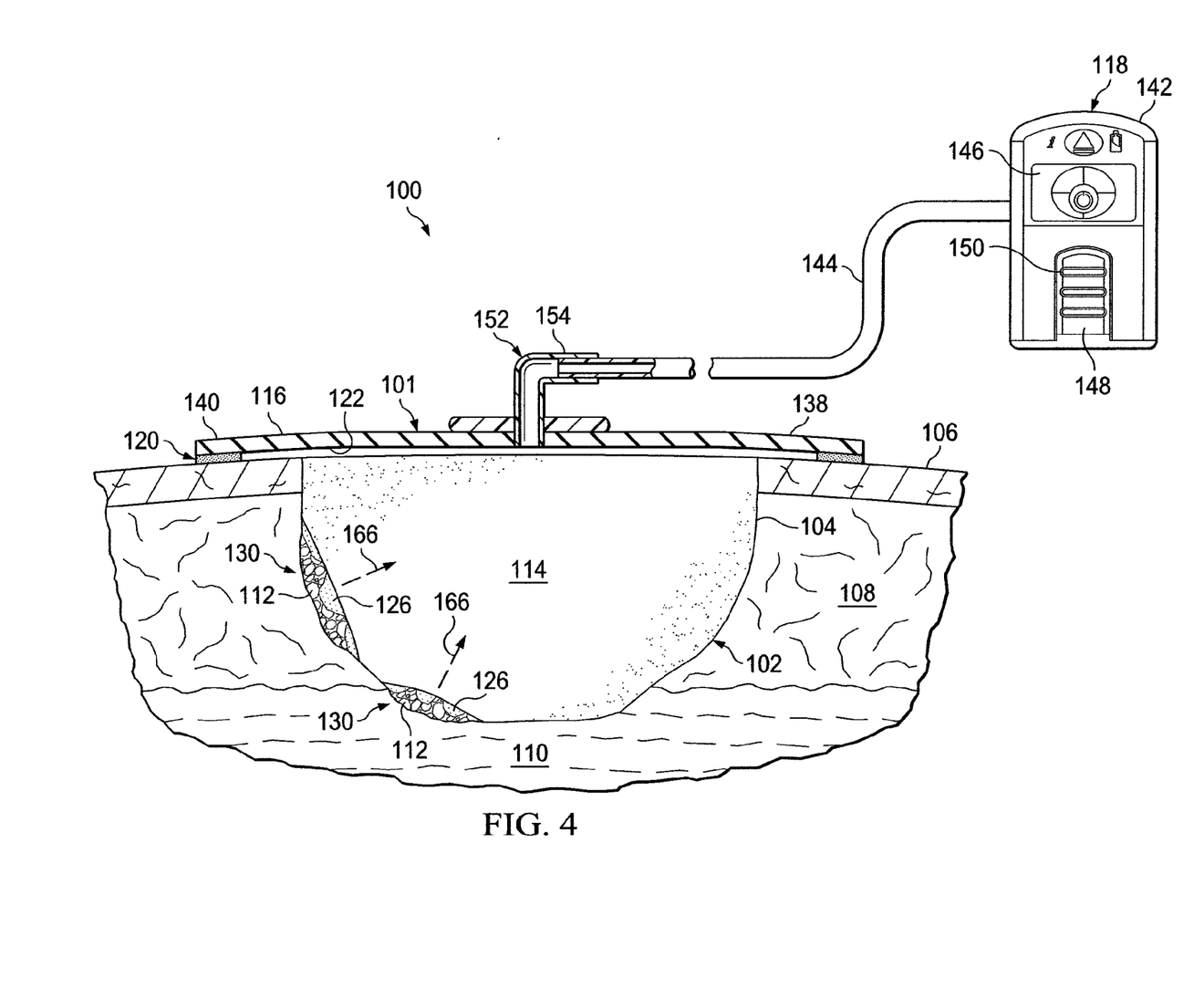
FIG. 4 is a schematic, side view, with a portion shown in cross section, of a wound bed being treated by the reduced-pressure treatment system of FIG. 1, shown with the hydrogel softened.

Referring now primarily to FIG. 4, the presence of exudate causes the hydrogel 126 to soften and break apart over time. As the hydrogel 126 breaks apart, the manifold 114 and reduced-pressure source 142 function to remove the softened hydrogel 126 from the wound 104 as suggested by the directional arrows 166 of FIG. 4. Similarly, as the hydrogel 126 is removed from the wound, debrided tissue, or necrotic tissue 112, may be left uncovered by hydrogel and drawn into the manifold 114 of the reduced-pressure wound dressing 101. After the debrided tissue, e.g., necrotic tissue 112, is drawn into the manifold 114, the debrided tissue may be removed from the tissue site along with the manifold 114, as shown in FIG. 5. Accordingly, the reduced-pressure treatment system 100 has the advantages of using autolytic debridement to debride a treatment area 130, functioning as a dressing that allows for the accelerated and painless removal of softened debrided tissue, and simultaneously applying negative pressure therapy to the wound 104.

In an illustrative method for debriding a treatment area 130 at a tissue site 102 using, for example, the reduced-pressure treatment system 100 of FIG. 1, a caregiver may prepare the wound 104 by removing any loose material with irrigation. The caregiver identifies the areas to be debrided, i.e., treatment areas 130, and covers the areas with the hydrogel 126, as shown in FIG. 2. The wound 104 is further covered with a manifold 114 and sealing drape 116 to facilitate the application of reduced-pressure wound therapy. The manifold 114 is fluidly coupled to a reduced-pressure source 142 via a reduced-pressure interface 152 and reduced-pressure conduit 144. The hydrogel 126 helps to promote a moist environment at the treatment area 130 and thereby enhances autolytic debridement.

Moreover, the application of reduced pressure by the reduced-pressure source 142 ensures close proximity of the hydrogel 126 to necrotic tissue 112 at the treatment area 130.

The application of reduced pressure gradually pulls the hydrogel 126 into the foam pore structure of the manifold 114 as the hydrogel 126 softens. In addition, softened necrotic tissue 112, e.g., softened eschar, that is loosened by the debriding process may also be pulled into the foam pores of the manifold 114 by the reduced-pressure. After a period of time (e.g., 2 to 5 days) the dressing is removed and the process is repeated as needed. Until the hydrogel 126 is absorbed by the reduced-pressure wound dressing 101, the hydrogel 126 isolates the necrotic tissue 112 from the porous foam of the manifold 114. The non-porous hydrogel does not transmit negative pressure, which may help to concentrate moisture around the necrotic tissue 112 of the treatment area 130. As the necrotic tissue 112 softens, pathways may form that help to push the softened necrotic tissue 112 and hydrogel 126 into the foam pores of the manifold 114. In cases where the necrotic tissue 112 is liquefied as a result of the debriding process, the liquefied tissue can be drawn deeper into the manifold 114 and passed into a wound fluid collection canister 148 of the reduced-pressure source 142.

Figure 6:
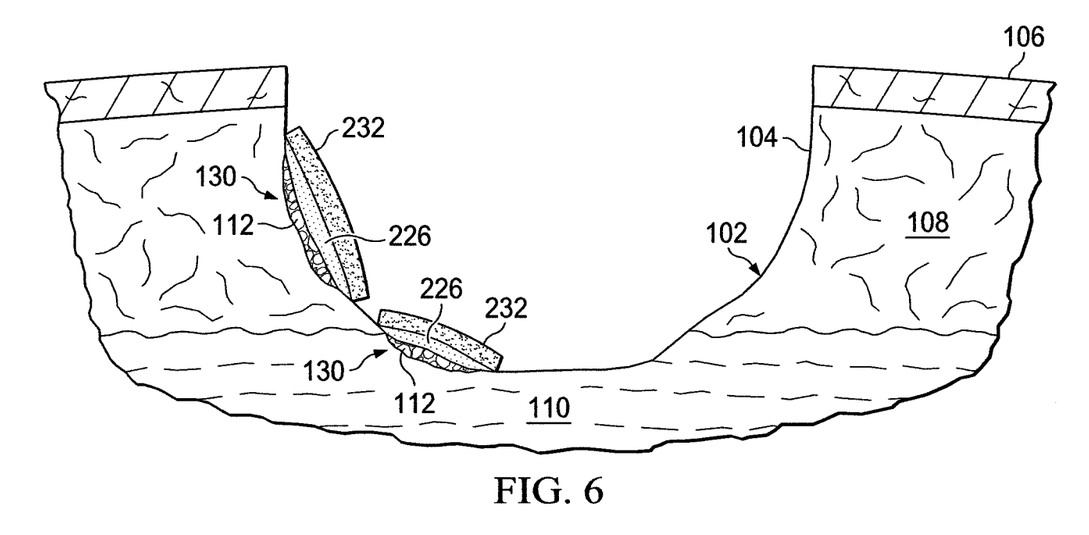
FIG. 6 is a schematic cross section, of a wound bed having necrotic tissue covered by a blocked acid debriding agent and intermediate foam layer.

Referring now primarily to FIG. 6, an illustrative embodiment is shown that isolates the hydrogel layer 226 from direct contact with the manifold 114. Here, an intermediate foam layer 232 may be placed adjacent the hydrogel 226 before applying a distribution manifold (not explicitly shown) to substantially cover the hydrogel 226. The intermediate foam layer 232 functions to delay the removal of the hydrogel 226 from the treatment area 130—even after the hydrogel 226 begins to soften.

The intermediate foam layer 232 may be a heat and moisture exchange (HME) foam. Further, the intermediate foam layer 232 may be hydrophilic polyurethane and may have a substantially smaller pore size than that of the manifold 114. The intermediate foam layer 232 may have a pore size of 60-100 pores per inch (PPI), and therefore may be more easily occluded by the hydrogel 226 than the manifold 114. In such an embodiment, the hydrogel 226 undergoes more softening before the hydrogel 226 can permeate the intermediate foam layer 232 than the hydrogel 226 would before it could permeate the manifold 114 with larger pores. The occluded foam also resists the transmission of reduced pressure thereby allowing the intermediate foam layer 232 to further isolate a treatment area 130 from the application of reduced pressure.

It is noted that while the hydrogel 226 and intermediate foam layer 232 are shown in FIG. 6 as treating discrete treatment areas 130 that include necrotic tissue 112, the hydrogel 226 and intermediate foam layer 232 may also be applied to other portions of the tissue site 102, including the entirety of a wound 104. The hydrogel 126 of FIG. 1 may be similarly applied. In some cases, the majority or all of the wound bed may have a layer of necrotic tissue 112 that should be debrided to improve wound health.

Figure 7:
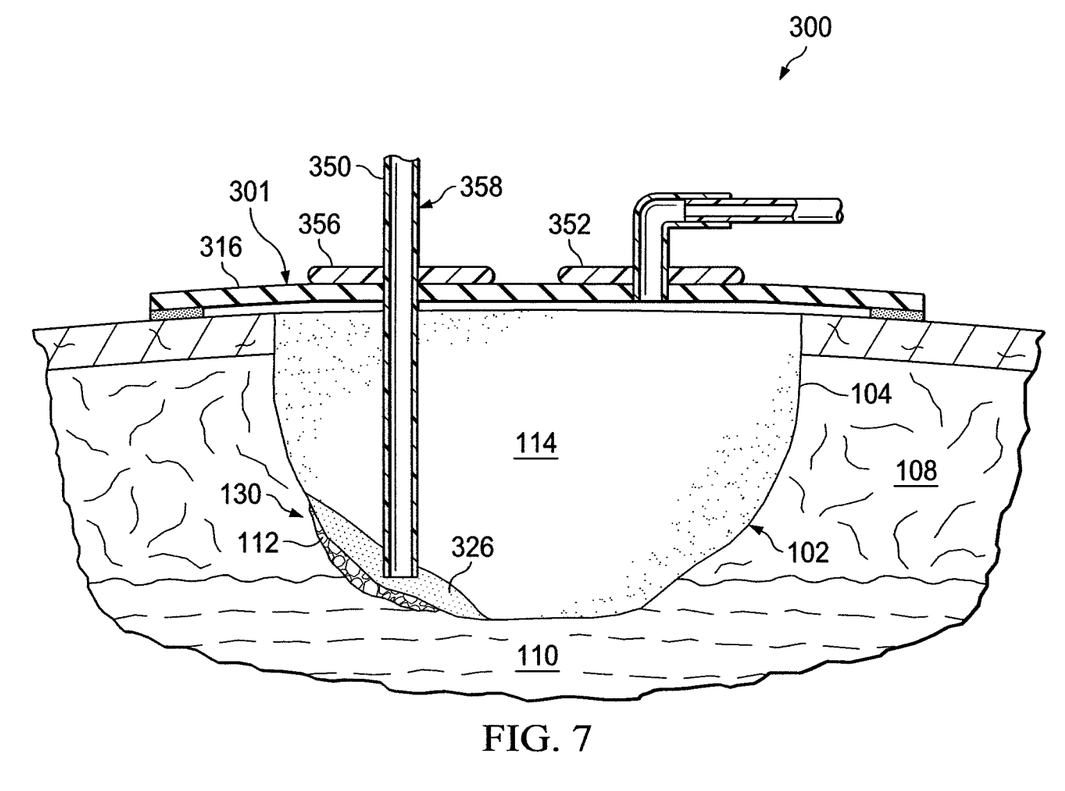
FIG. 7 is a schematic cross section, of a reduced-pressure treatment system employing enhanced autolytic debridement to remove necrotic tissue from a wound.
Figure 8:
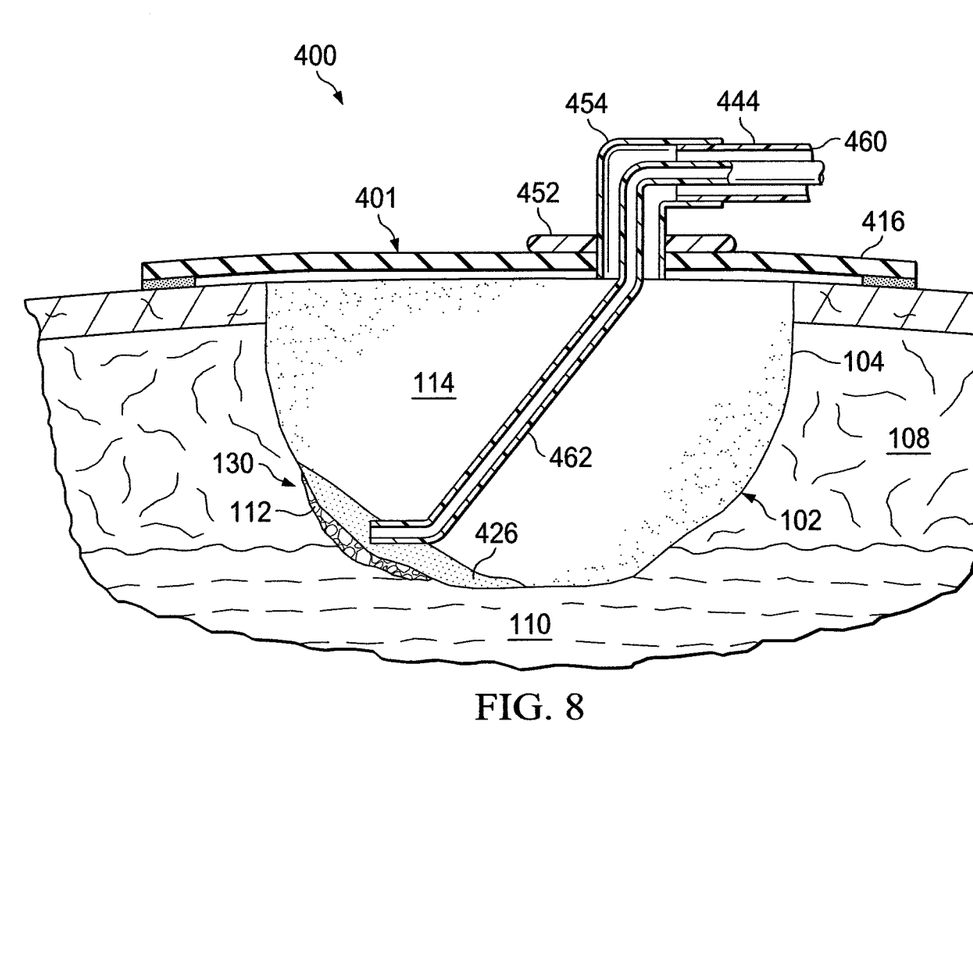
FIG. 8 is a schematic cross section, of a reduced-pressure treatment system employing enhanced autolytic debridement to remove necrotic tissue from a wound.

Referring now primarily to FIGS. 7 and 8, in another illustrative embodiment, a hydrogel 326, 426 may be injected into the wound 104 at the treatment area 130 after a reduced-pressure wound dressing 301, 401 has been applied to the tissue site 102. FIGS. 7 and 8 show illustrative reduced-pressure debridement systems that enable the caregiver to inject a hydrogel 326, 426 to facilitate enhanced autolytic debridement after the application of a reduced-pressure wound dressing 301, 401.

Referring now primarily to FIG. 7, a system 300 is presented in which the manifold 114 has already been applied to the tissue site 102. The system 300 includes a sealing drape 316 and a reduced-pressure interface 352 to fluidly couple the manifold 114 to a reduced-pressure source. A second interface 356 is affixed to the sealing drape 316 to allow a second port 358 and second conduit 350 to deliver the hydrogel 326 to the treatment area 130. The hydrogel 326 may be less viscous when it is supplied to the treatment area 130 of a tissue site 102. The hydrogel 326 may be adapted to absorb fluid and become more viscous when the hydrogel 326 contacts fluids exuded from the wound 104. In another embodiment, the hydrogel 326 may be introduced to the tissue site using a syringe with an applicator needle (not shown). An example of a hydrogel 326 that is adapted to increase in viscosity when in contact with a liquid (e.g., water) is a super-absorbent polymer dispersed within a paraffin.

Referring now primarily to FIG. 8, a system 400 that is similar in many respects to the system 300 of FIG. 7 is presented. FIG. 8 shows a system 400 in which the hydrogel 426 may be supplied to the treatment area 130 of a tissue site 102 through a reduced-pressure interface 452. The reduced-pressure interface 452 accommodates a dual lumen conduit 444 through an elbow port 454 or similar port that is coupled to the sealing drape 416. The dual lumen conduit 444 includes a first lumen 460 and a second lumen 462. The first lumen 460 supplies reduced pressure to the tissue site 102. The second lumen 462 is adapted to deliver a hydrogel 426 to the tissue site 102 to define a treatment area 130. Again, the hydrogel 426 may be suspended in a non-absorbing liquid carrier (i.e. the hydrogel will not absorb the carrier liquid), such as paraffin, that permits the suspended hydrogel to thicken when in contact with wound fluid, thereby increasing the viscosity of the hydrogel 426 and adapting the hydrogel 426 to define a treatment area 130 that is a moisture-rich environment and therefore conducive to debridement. Contemporaneously, reduced pressured may be delivered to the tissue site 102 to provide reduced-pressure wound therapy to the remainder of the tissue site 102.

In another illustrative embodiment, the hydrogel may be impregnated with one or more chemicals that accelerate the debridement process, or infused with an antimicrobial agent to treat an infected wound for which debridement is not recommended. In another embodiment, the hydrogel is replaced with a porous hydrophilic foam. The porous hydrophilic foam will help maintain a moist environment to encourage autolytic debridement and simultaneously apply reduced pressure to a treatment area. The use of a hydrophilic foam at the treatment area may provide enhanced ability to control fluid in high exuding wounds that require debriding.

The wound dressings and systems disclosed herein may offer a number of advantages for patients and caregivers. For example, the wound dressings and systems disclosed herein address the problem of causing pain to a patient by other debridement techniques, e.g., a mechanical or chemical debridement procedure, and thereby may reduce the need for the application of anesthetics. The illustrative methods, systems and wound dressings target only necrotic tissue for debridement, and apply negative pressure therapy to healthy portions of a wound. In addition, unlike traditional debriding agents, application of a hydrogel having a blocked acid debridement agent to healthy tissue will not cause an adverse reaction. In addition, the systems and methods disclosed herein may allow the caregiver to spend less time on the specific task of debridement by completing the task using reduced-pressure wound dressing materials that may already be treating and protecting the wound. From a patient's point of view, the illustrative enhanced autolytic debridement method involves less pain and requires one less trip to the operating room for a debridement procedure.

According to another illustrative embodiment, a self-contained wound dressing analogous to those previously presented may be used that does not require the need for an external reduced-pressure source, reduced-pressure conduit, or an external fluid collection canister. For example, a wound dressing may be formed to include a reduced-pressure source, such as a micro-pump, to generate reduced-pressure at the tissue site, thereby eliminating the need for an external reduced-pressure source. In addition, a dressing may include an absorbent or superabsorbent pouch that is isolated from the manifold by one or more wicking layers to perform the function of the fluid collection canister 148 of FIG. 1. In an embodiment having a fluid collection reservoir and a reduced-pressure source internal to the wound dressing, the system, which is otherwise analogous to the illustrative system of FIG. 1, may be contained entirely within a reduced-pressure wound dressing.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples, and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A reduced-pressure treatment system for debriding a treatment area of a tissue site, the system comprising:
   a hydrogel adapted to cover the treatment area, wherein the hydrogel comprises a blocked acid debriding agent comprising an alpha hydroxy acid bound to a blocking material;
   a manifold adapted to cover the hydrogel and distribute reduced pressure to the tissue site; and
   a sealing drape for placing over the tissue site and manifold, the sealing drape adapted to form a fluid seal over the tissue site and manifold;
   a reduced-pressure interface for delivering reduced pressure to the manifold; and
   a reduced-pressure subsystem for providing reduced pressure.

2. The reduced-pressure treatment system of claim 1, wherein the blocked acid debriding agent comprises lactic acid and an arginine group.

3. The reduced-pressure treatment system of claim 1, wherein the blocked acid debriding agent comprises glycolic acid and arginine.

4. The reduced-pressure treatment system of claim 1, wherein the hydrogel is adapted to soften and break apart over time in response to exposure to wound fluid.

5. The reduced-pressure treatment system of claim 4, wherein the manifold is adapted to absorb the hydrogel after the hydrogel softens.

6. The reduced-pressure treatment system of claim 1, wherein the manifold is adapted to absorb debrided necrotic tissue.

7. The reduced-pressure treatment system of claim 1, wherein the hydrogel is a viscous gel.

8. The reduced-pressure treatment system of claim 1, further comprising an intermediate foam layer between the hydrogel and the manifold.

9. A method of manufacturing a reduced-pressure wound dressing for treating a tissue site and debriding a treatment area, the method comprising:
providing a hydrogel,
wherein the hydrogel is adapted to cover the treatment area, and
wherein the hydrogel comprises a blocked acid debriding agent comprising an alpha hydroxy acid bound to a blocking material;
providing a manifold, wherein the manifold is adapted to cover the hydrogel and distribute reduced pressure to the tissue site;
providing a sealing drape for placing over the tissue site and manifold, the sealing drape adapted to form a fluid seal over the tissue site and manifold;
providing a reduced-pressure interface for delivering a reduced pressure to the manifold; and
providing a reduced-pressure subsystem.

10. The method of claim 9, further comprising providing an intermediate foam layer for disposing between the hydrogel and the manifold.

11. The method of claim 9, wherein the hydrogel is adapted to soften and break apart over time in response to exposure to wound fluid.

12. The method of claim 9, wherein the manifold is adapted to absorb the hydrogel after the hydrogel softens.

13. A method for treating a tissue site on a patient, the method comprising:
defining a treatment area by applying a hydrogel to a portion of the tissue site, wherein the treatment area comprises tissue to be debrided and the hydrogel comprises a blocked acid debriding agent comprising an alpha hydroxy acid bound to a blocking material;
applying a manifold over the hydrogel, wherein the manifold is adapted to deliver reduced-pressure to the tissue site;
applying a sealing drape over the tissue site and manifold to form a fluid seal over the tissue site and manifold; and
providing reduced pressure to the manifold.

14. The method of claim 13, wherein the tissue to be debrided comprises a tissue selected from a group consisting of necrotic tissue, damaged tissue, infected tissue, contaminated tissue, and adherent tissue.

15. The method of claim 13, further comprising debriding the tissue to be debrided for more than two days.

16. The method of claim 13, wherein applying the hydrogel to the portion of the tissue site comprises applying a hydrogel from a tube.

17. A reduced-pressure wound dressing comprising:
a hydrogel adapted to cover a treatment area of a tissue site, wherein the hydrogel comprises a blocked acid debriding agent comprising an alpha hydroxy acid bound to a blocking material;
a manifold adapted to cover the hydrogel and distribute reduced pressure to the tissue site; and
a sealing drape for placing over the tissue site and manifold, the sealing drape adapted to form a fluid seal over the tissue site and manifold.

18. The reduced-pressure wound dressing of claim 17, further comprising an intermediate foam layer between the hydrogel and the manifold.

19. The reduced-pressure wound dressing of claim 17, wherein the blocked acid debriding agent comprises lactic acid and arginine.

20. The reduced-pressure wound dressing of claim 17, wherein the blocked acid debriding agent comprises glycolic acid and arginine.

21. The reduced-pressure wound dressing of claim 17, wherein the hydrogel is adapted to soften and break apart over time in response to exposure to wound fluid.

22. The reduced-pressure wound dressing of claim 17, wherein the manifold is adapted to absorb the hydrogel after the hydrogel softens.

23. The reduced-pressure wound dressing of claim 17, wherein the manifold is adapted to absorb debrided necrotic tissue.

24. The reduced-pressure wound dressing of claim 17, wherein the hydrogel is a preformed sheet.

25. The reduced-pressure wound dressing of claim 17, wherein the hydrogel is a viscous gel.

* * * * *